(12) United States Patent
Haxo et al.

(10) Patent No.: US 11,092,595 B2
(45) Date of Patent: Aug. 17, 2021

(54) USE OF BISPYRIDINES TO IMPROVE LABELING OF NUCLEOPHILES

(71) Applicant: Agilent Technologies, Inc., Santa Clara, CA (US)

(72) Inventors: Francis T. Haxo, San Francisco, CA (US); Michael J. Kimzey, Laguna Hills, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 28 days.

(21) Appl. No.: 16/072,816

(22) PCT Filed: Feb. 24, 2017

(86) PCT No.: PCT/US2017/019346
§ 371 (c)(1),
(2) Date: Jul. 25, 2018

(87) PCT Pub. No.: WO2017/147417
PCT Pub. Date: Aug. 31, 2017

(65) Prior Publication Data
US 2019/0041384 A1 Feb. 7, 2019

Related U.S. Application Data

(60) Provisional application No. 62/300,609, filed on Feb. 26, 2016.

(51) Int. Cl.
| | | |
|---|---|---|
| *G01N 33/533* | (2006.01) | |
| *C07D 207/46* | (2006.01) | |
| *C07D 213/24* | (2006.01) | |
| *C12Q 1/6806* | (2018.01) | |
| *C07H 1/00* | (2006.01) | |

(52) U.S. Cl.
CPC ......... *G01N 33/533* (2013.01); *C07D 207/46* (2013.01); *C07D 213/24* (2013.01); *C07H 1/00* (2013.01); *C12Q 1/6806* (2013.01); *G01N 2560/00* (2013.01)

(58) Field of Classification Search
CPC .... G01N 33/533; G01N 2560/00; C07H 1/00; C07D 207/46; C07D 213/24; C12Q 1/6806
See application file for complete search history.

(56) References Cited

U.S. PATENT DOCUMENTS

| | | | | |
|---|---|---|---|---|
| 5,162,508 | A * | 11/1992 | Lehn ..................... | C07D 471/22 436/546 |
| 5,648,270 | A * | 7/1997 | Kuhn ..................... | C09K 11/06 436/172 |
| 6,514,767 | B1 | 2/2003 | Natan | |
| 6,696,304 | B1 * | 2/2004 | Davies ............. | G01N 33/54346 435/4 |
| 2008/0305489 | A1 | 12/2008 | Thomas | |
| 2009/0258437 | A1 * | 10/2009 | Baginski ............... | C07D 207/46 436/501 |
| 2012/0107942 | A1 | 5/2012 | Baginski | |
| 2012/0183954 | A1 * | 7/2012 | Diwu ..................... | C09B 11/24 435/6.1 |

FOREIGN PATENT DOCUMENTS

| | | |
|---|---|---|
| CN | 103267819 | 8/2013 |
| EP | 1775729.9 | 4/2019 |
| JP | H6(1994)-065300 A | 1/1994 |
| JP | 2003-511557 A | 3/2003 |
| JP | 2013-539015 A | 10/2013 |
| WO | PCT/US2017/019346 | 5/2017 |

OTHER PUBLICATIONS

Zhou et al. Synthesis, labeling and bioanalytical applications of a tris(2,2'-bipyridyl)ruthenium(II)—based electrochemiluminescence probe. Nature Protocols 2014, vol. 9, No. 5, pp. 1146-1159. (Year: 2014).*
Kaur, P., et al., "Multi-signalling cation sensing behavior of a bis(pyridin-2-yl methyl) aniline based hetarylazo dye," Analytica Chemica Acta, 2013, pp. 79-86, vol. 778.
Lauber, M, et. al, "Rapid preparation of released N-glycans for HILIC analysis using a novel fluorescence and MS-active labeling reagent," 2015, XP055624648.
Bender, Myron, "Mechanisms of catalysis of nucleophilic reactions of carboxylic acid derivatives," Chemical Rev., 1960, pp. 53-113, vol. 60.
Anonymous, "Bipyridine," 2015, Wikipedia, XP055627702.
Tep, Samnang, "The Development and Application of a MALDI-TOF MS Method for Quantitative Glycomic Anal," Dissertation, Northeastern Univ, Nov. 2011, pp. 1-202, p. 202, para 1.
Kimzey et al., "Development of an Instant Glycan Labeling Dye for High Throughput Analysis by Mass Spectrometry" Bulletin, 2003, pp. 1-4, p. 1, Summary, p. 2, Figure 1, para 1.

* cited by examiner

*Primary Examiner* — Shafiqul Haq
(74) *Attorney, Agent, or Firm* — Laurence J. Hyman; Hyman IP Law

(57) ABSTRACT

Bispyridines improve the labeling of nucleophiles, including amines and thiols and are particularly useful for improving labeling with acidic and basic labels. Use of bispyridines with such labels dramatically increases labeling compared to protocols without a bispyridine. The labeled nucleophile can then be subjected to standard analytical methods.

13 Claims, 3 Drawing Sheets

USE OF BISPYRIDINES TO IMPROVE LABELING OF NUCLEOPHILES

CROSS-REFERENCE TO RELATED APPLICATIONS

This application is a national stage application under 35 U.S.C. § 371 of International Application No. PCT/US2017/019346, filed Feb. 24, 2017, which is hereby incorporated by reference. This application further claims the benefit of, and priority to, U.S. Provisional Patent Application No. 62/300,609, filed Feb. 26, 2016, the contents of which are incorporated herein by reference for all purposes.

STATEMENT OF FEDERAL FUNDING

Not applicable.

BACKGROUND OF THE INVENTION

This invention relates to the field of improving labeling of nucleophilic biomolecules by electrophilic labels, and particularly to labeling glycosylamines.

Many of the proteins produced by eukaryotic cells are modified after translation by the addition of covalently-linked, linear or branched chains of carbohydrates. These protein-carbohydrate conjugates are referred to as glycoproteins; the point at which the carbohydrate is attached is referred to as a glycosylation site. Attached polysaccharides or oligosaccharides are referred to as glycans. A wide range of glycans are found on the different glycosylation sites of particular glycoproteins. The particular pattern of glycans on a particular glycoprotein is determined by the specific cell line that produced the protein and the conditions under which the cells were grown.

Since the glycans conjugated to a protein can affect characteristics critical to its function, including pharmacokinetics, stability, bioactivity, or immunogenicity, it is important in many uses to determine which glycans are present. Thus, the ability to remove some or all of the glycans from a protein and to analyze the glycans to determine their composition is useful for determining whether the glycoprotein will have its desired effect. For example, the Food and Drug Administration ("FDA") requires characterization of carbohydrates attached to biologics (such as therapeutic glycoproteins and vaccines) to show composition of matter and consistency of manufacture, resulting in a need for extensive characterization of the product. Analysis of the profile of the released carbohydrates is also important for quality control in the production of recombinant proteins, in which a change in carbohydrate profile may indicate stress in the system, signaling conditions that may require a commercial-scale fermenter of expensive protein to be discarded. There is therefore considerable interest by biochemists, clinical chemists and pharmaceutical manufacturers in determining the distribution profiles of glycans in biological samples, such as therapeutic glycoproteins.

Glycans are typically attached to glycoproteins in one of two ways. In the first, referred to as N-glycans, the glycans are attached through an N-glycosidic bond at an asparagine residue. In the second, referred to as O-glycans, glycans are attached to an oxygen atom on an amino acid residue. For example, N-acetyl-galactosamine can be enzymatically attached to an oxygen on a serine or a threonine residue.

N-glycans can be enzymatically released from glycoproteins by enzymatic cleavage by various enzymes, such as PNGase F (Peptide-N4-(acetyl-β-glucosatninyl)-asparagine amidase, EC 3.5.1.52.). Release of glycans from a glycoconjugate, such as a glycoprotein, by an enzyme is sometimes referred to in the art as "enzymatic digestion." Enzymatic digestion of N-glycans, such as by PNGase F, typically occurs in an aqueous solution, and results in the initial release of the N-glycans as β-glycosylamines, in which the free-reducing end of the released glycan is conjugated with ammonia (see, e.g., Tarentino, et al. TIGG 1993, 23:163-170; Rasmussen J. R. J. Am. Chem. Soc. 1992, 114:1124-1126; Risley, et al. J. Biol. Chem. 1985, 260: 15488-15494, 1985). PNGase F-released N-glycans are most commonly labeled by reductive amination, in which the free-reducing end of a glycan is conjugated to the free amino group of a label, such as a fluorescent dye or a electrical charge. Depending on the label used, the labeled glycans can then be analyzed by any of a variety of analytical methods, such as high-performance liquid chromatography ("HPLC"), capillary electrophoresis ("CE"), carbohydrate gel electrophoresis, or microfluidic separation. Labeling of N-glycans is taught, for example, in co-owned U.S. Pat. Nos. 8,124,792 and 8,445,292.

The stability of glycosylamines is dependent on the pH: a lower pH favors rapid hydrolysis of glycosylamines to glycans with free-reducing ends and ammonium, while a more elevated pH slows glycosylamine hydrolysis, which allows glycans released as glycosylamines to be labeled with reagents reactive toward the amino groups instead of the free-reducing ends. Thus, the released glycosylamines are both more stable and more reactive with labeling reagents within a pH range of about pH 7.5 to about pH 9. Unfortunately, many of the amine-reactive dyes compatible with different analytical techniques are either acidic or basic and are more stable at pHs lower than 6. This dichotomy between the conditions most favorable for stability of the glycosylamines and those most favorable for stability of a basic or an acidic dye can cause incomplete labeling of glycans released from glycoproteins by enzymatic digestion.

There remains a need in the art for compositions and methods that improve labeling of glycosylamines and other nucleophiles. Surprisingly, the present invention meets these and other needs.

BRIEF SUMMARY OF THE INVENTION

In some embodiments, the invention provides methods of labeling a nucleophile of interest in vitro. The methods comprise the step of incubating the nucleophile with a solution comprising (a) a solvent, (b) an electrophilic label reactive with the nucleophile, and (c) a bispyridine soluble in the solvent, thereby labeling the nucleophile. In some embodiments, the nucleophile is an amine. In some embodiments, the amine is a glycosylamine. In some embodiments, the glycosylamine is released from a glycoprotein prior to the incubation step. In some embodiments, the release of the glycosylamines from the glycoprotein is by enzymatic digestion. In some embodiments, the enzymatic digestion of said glycoprotein comprises digestion by the enzyme PNGase F. In some embodiments, the nucleophile is a thiol. In some embodiments, the nucleophile is a guanidine or an imidazole group on a protein or peptide. In some embodiments, the nucleophile is an exocyclic amine on a nucleic acid. In some embodiments, the bispyridine is pyridine, 4,4'-(1,3-propanediyl)bis- or pyridine, 4,4'-(1,2-ethanediyl) bis-. In some embodiments, the solvent is dimethylforamide or dimethyl sulfoxide. In some embodiments, the electrophilic label is acidic in aqueous solution. In some embodiments, the electrophilic label is basic in aqueous solution.

In some embodiments, the invention further provides methods for labeling N-glycans released from a glycoprotein of interest. The methods comprise (a) incubating the glycoprotein with an enzyme that releases the N-glycans from the glycoprotein as glycosylamines, and (b) contacting the glycosylamines with a solution comprising a solvent, an amine-reactive label, and a bispyridine, under conditions allowing labeling of the glycosylamines by the amine-reactive label, thereby labeling the N-glycans released from the glycoprotein. In some embodiments, the glycoprotein is an antibody. In some embodiments, the glycoprotein is immobilized on a solid support before step (b). In some embodiments, the deglycosylation enzyme is an endoglycosidase. In some embodiments, the deglycosylation enzyme is an amidase. In some embodiments, the amidase is PNG F. In some embodiments, the solvent is dimethylforamide or dimethyl sulfoxide. In some embodiments, the bispyridine is pyridine, 4,4'-(1,3-propanediyl)bis- or pyridine, 4,4'-(1,2-ethanediyl)bis-. In some embodiments, the labeled glycosylamines are analyzed by an analytical means. In some embodiments, the analytical means is selected from the group consisting of high-pressure liquid chromatography, capillary electrophoresis, microfluidic separation, and mass spectrometry.

In some embodiments, the invention further provides kits for labeling a nucleophile of interest. The kits comprise (a) a bispyridine, (b) a label reactive with the nucleophile of interest, and (c) instructions on labeling the nucleophile. In some embodiments, the nucleophile is a glycosylamine. In some embodiments, the label is an amine-reactive dye. In some embodiments, the bispyridine is pyridine, 4,4'-(1,3-propanediyl)bis- or pyridine, 4,4'-(1,2-ethanediyl)bis-. In some embodiments, the label is dry 2-(diethylamino)ethyl 4-[(2,5-dioxopyrrolidin-1-yl)oxycarbonylamino]benzoate and said bispyridine is pyridine, 4,4'-(1,3-propanediyl)bis- or pyridine, 4,4'-(1,2-ethanediyl)bis-. In some embodiments, the bispyridine is in a solvent. In some embodiments, the solvent is dimethylforamide.

DETAILED DESCRIPTION

Figure 1:
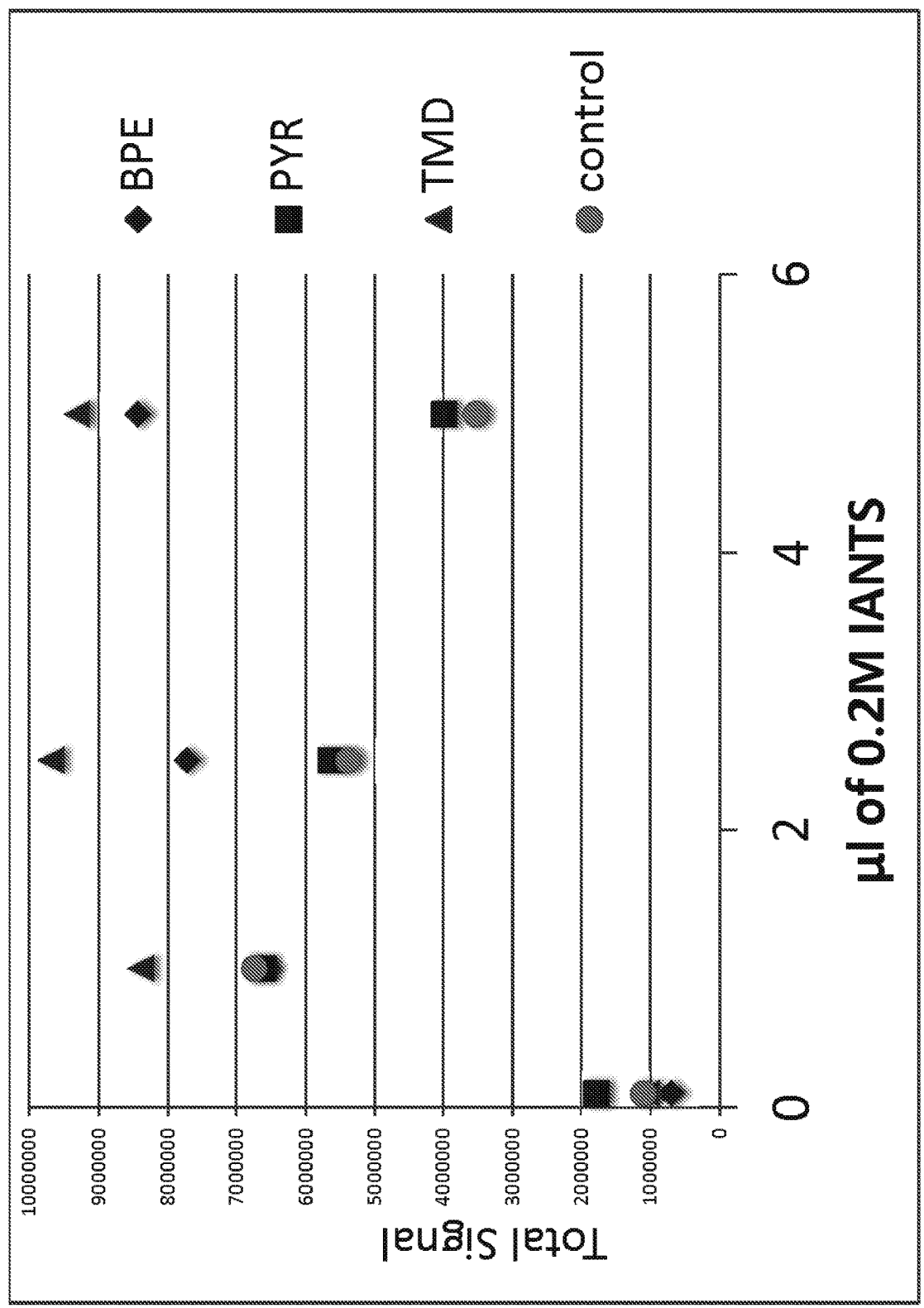
FIG. 1 is a graph showing the total glycan signal of glycosylamines released by PNGase F from an exemplar glycoprotein, porcine gamma globulin, and labeled by an acidic dye, 8-[(2,5-dioxopyrrolidin-1-yl)oxycarbonylamino]naphthalene-1,3,5-trisulfonic acid, in the presence of 1 M pyridine ("PYR", represented by squares), 1 M Pyridine, 4,4'-(1,2-ethanediyl)bis- ("BPE", represented by diamonds), or 1 M Pyridine, 4,4'-(1,3-propanediyl)bis- ("TMD", represented by triangles). Each of these chemicals was dissolved in anhydrous dimethyl sulfoxide ("DMSO") as the solvent. The control, represented by circles, was the DMSO solvent without pyridine or a bispyridine. Vertical axis: total glycan signal, in relative fluorescence units ("RFUs"), measured at 430 nm. Horizontal axis: number of microliters of the dye ("ANTS") present in the assay. The amounts of dye used were: 0.1 µl, 1 µl, 2.5 µl, and 5 µl.

As set forth in the Background, analysis of the glycans attached to glycoproteins has become important for meeting various regulatory requirements, including showing composition of matter and consistency of manufacture of therapeutic glycoproteins and for providing quality control during the production of recombinant glycoproteins. As further described in the Background, N-glycans are typically analyzed by releasing them by enzymatic digestion and then labeling the resulting glycosylamines with an amine-reactive dye. Unfortunately, while the glycosylamines released from glycoproteins are both more stable and more reactive with labeling reagents within a pH range of about pH 7.5 to about pH 9, many of the amine-reactive dyes used for labeling glycosylamines are either acidic or basic and are more stable at pHs lower than 6. At higher pHs, such as above pH 9, the glycosylamines are stable but the nucleophile-reactive tags hydrolyze rapidly, especially if water is the primary solvent. Therefore, it is advantageous to neutralize the amine-reactive dyes prior to addition to the glycosylamines. This dichotomy between the conditions most favorable for stability of the glycosylamines and those most favorable for stability of a basic or an acidic dye reduces the ability to get complete labeling of glycans released from glycoproteins by enzymatic digestion.

Despite this dichotomy, buffers are currently not typically added to the organic solvent portion in labeling protocols. Typical protocols recommend the buffering of the aqueous solution only, i.e. with a buffer such as sodium carbonate pH 7-9. These protocols generally apply to stable nucleophiles such as primary amines and do not factor in the transient nature of glycosylamines, which are rapidly hydrolyzed at low pH. This may be because common laboratory buffers, such as phosphate buffered saline, are aqueous solutions which themselves hydrolyze amine reactive dyes and other labels. If aqueous-solution buffers were to be used, therefore, they would have to be added to the amine reactive label or dye immediately before or after the label or dye is added to the solution containing the glycans. As any delay in buffering could result in some of the glycosylamines being hydrolyzed before they can be labeled, the timing of adding such a buffer itself could introduce undesirable variation in the measurement of the glycans present in the solution. It is preferred to buffer the electrophilic label prior to labeling the aqueous nucleophile. Further, a number of amine-reactive dyes or other labels are sold as powders, which are resolubilized by the user and then stored until use, either as is or, when additional storage life is desired, in a freezer. It is therefore more convenient for the user if the buffer can be added at the time the dye is first resolubilized thereby avoiding an additional time-critical step during the labeling protocol. Aqueous-solution buffers are incompatible with being added to resolubilized amine reactive dyes in advance of use for the reasons noted above.

Surprisingly, it has now been found that bispyridines, commonly used in polymer chemistry, dramatically improve the labeling of glycosylamines with acidic or basic dyes compared to current labeling protocols. As shown below and in the Examples, studies using two different bispyridines, two different acidic amine-reactive dyes and a basic amine-reactive dye, and two different solvents, showed that the presence of bispyridines during the labeling procedure resulted in a surprisingly more complete labeling of glycosylamines than did the standard labeling procedure without a bispyridine being present.

FIG. 1 presents the results of studies were performed using an acidic amine-reactive dye to label glycosylamines released from an exemplar glycoprotein in the presence of (a) the bispyridine Pyridine, 4,4'-(1,2-ethanediyl)bis- ("BPE," compound 1 in the list of bispyridines below) prepared in anhydrous DMSO, (b) the bispyridine 4,4'-(1,3-propanediyl)bis-pyridine ("TMD," compound 2 in the list of structures in the section on bispyridines below), prepared in anhydrous DMSO, (c) pyridine ("PYR") in DMSO, or (d) DMSO without pyridine or a bispyridine ("control"). As shown in FIG. 1, the use of pyridine in DMSO resulted in glycan labeling approximately the same as that of the DMSO-only control. In contrast, once enough label (2.5 µl) was present to provide relatively adequate labeling, the presence of TMD resulted almost doubled the amount of glycosylamines labeled compared to the control and pyridine solutions, while when 5 µl of dye was used, the presence of either TMD or BPE resulted in labeling over twice as much glycan compared to mixtures containing either pyridine or the DMSO control.

Without wishing to be bound by theory, it is believed that the presence of the bispyridine buffers the solution and stabilizes the glycosylamines, the amine-reactive dye, or both, allowing a larger amount of the glycosylamines to be labeled before they or the dye were hydrolyzed. The results may not, however, be explainable by a buffering action alone, as the glycosylamines were released from the glycoprotein by enzymatic digestion with the enzyme PNGase F in a solution containing the buffer HEPES at pH 8, and that buffer was already present in each of the samples then subjected to labeling with the dye.

Based on the studies underlying embodiments of the present invention, it is believed that bispyridines can be used to improve the labeling by electrophilic labels of nucleophiles, including amines and thiols, as well as guanidine and imidazole groups on proteins and peptides and exocyclic amines on nucleic acids. In some embodiments, the labeling is of amines with amine-reactive dyes, In some embodiments, the labeling is of thiols with thiol-reactive dyes. In some embodiments, the nucleophile is an amine. In some embodiments, the nucleophile is a thiol. The label can be one that can be detected optically, such as a fluorescent dye, or that can add a fixed charge that is detectable by MS or that can facilitate separation and detection of the labeled moiety by electrokinetic separation techniques such as capillary electrophoresis.

Further studies underlying embodiments of the present invention revealed some differences exist between the ability of different bispyridines in different solvents or to undergo freezing in a solvent. In preferred embodiments, the bispyridine selected is soluble at room temperature in the solvent in which the dye is soluble. Since, as noted above, water hydrolyzes amine-reactive dyes, for uses in which storage of the dye-bispyridine mixture is desired, the solvent is preferably not water.

Studies found, for example, that the exemplar bispyridines TMD and BPE discussed above are both soluble in DMSO, and that TMD is also soluble in the solvent dimethylformamide ("DMF"). Another bispyridine studied, 4,4'-methylenebis-pyridine (compound 21 in the list set forth below), was not soluble in DMF, but is expected to be soluble in other organic solvents usable in some labeling procedures, such as dimethyl sulfoxide. The bispyridine BPE, which, as discussed above dramatically increases labeling of glycans over a like mixture not containing a bispyridine, was soluble in an aqueous solution. This bispyridine, however, came out of solution when frozen and did not go back into solution when the dye-bispyridine mixture was thawed. This bispyridine is therefore very useful for embodiments in which the practitioner does not need to store the mixture by freezing it, but less preferred for embodiments in which the user wishes to extend the storage life by freezing the mixture.

Bispyridines can also be used to label glycosylamines released from O-glycans by, for example, β-elimination. Further, bispyridines can be used in protocols to label thiols, such as the cysteines present in proteins or peptides. They may also be used to improve labeling of nucleophilic groups on proteins, such as the N-terminus (which can have a primary amine available for labeling), or lysine, arginine, or histidine, each of which nucleophilic groups available for labeling. Similarly, they may also be used to improve labeling of nucleophilic groups on nucleic acid bases such as the exocyclic amines of adenine and guanine. Finally, they may also be used to improve stability of electrophilic labels during storage while in solution. Persons of skill will appreciate that nucleophiles such as amines and thiols on proteins, peptides or nucleic acids can be labeled using the same protocols as discussed in the Examples using glycosylamines as an exemplar nucleophile to be labeled.

Any particular bispyridine can be readily tested to determine if it is soluble in a selected solvent at room temperature by simply mixing it with the selected solvent in a test tube and observing whether it goes into solution. Similarly, any particular bispyridine can be readily tested to determine if it is suitable for use in applications in which the user will freeze for later use a solution containing a selected dye in a selected solvent by placing the bispyridine in the selected solvent, freezing the resulting mixture, thawing it, and observing whether the bispyridine stays in solution upon freezing or, if it precipitates, whether it resolubilizes in the mixture upon being thawed. Further, any particular bispyridine can be readily tested to see if it improves storage of any particular electrophilic label in solution by (a) storing parallel aliquots of the label with and without the bispyridine (b) then testing them by adding excess of any of the nucleophiles mentioned above to each aliquot, (c) measuring the amount of labeled nucleophile, and (d) determining whether of the resulting amount of labeled nucleophile is greater or lesser in the aliquot with the bispyridine compared to the aliquot without the bispyridine.

The studies reported herein show that bispyridines are particularly useful when using labels that are acidic or basic in aqueous solutions. Labels that are neutral in aqueous solutions may act in ways that are not well characterized when dissolved in organic solvents, in which only trace amounts of water may be present. Any particular neutral label can be readily tested to determine whether it will label a nucleophile of interest better if a particular bispyridine is present than in its absence by testing parallel aliquots of the neutral label with and without the bispyridine, as described in the preceding paragraph.

Bispyridines

As suggested by the name, bispyridines are a class of compounds comprising two pyridine rings. As characterized by Wikipedia, pyridine rings are heterocyclic rings similar to benzene, but with one methane group replaced by a nitrogen. The compound pyridine has an unpleasant, fish-like odor and is hazardous. In contrast, bispyridines do not have unpleasant odors and are not flammable, making them significantly safer and more pleasant to work with than pyridine. As shown by FIG. 1, bispyridines are surprisingly better reagents in protocols for labeling glycosylamines (and by extension, other amines and nucleophiles) than pyridine is, with substantial improvements in labeling the glycosylamines with the amine reactive dye used in that study once adequate amounts of label were present.

Bispyridines are commonly used in polymer chemistry. A search of the SciFinder® database maintained by Chemical Abstract Services ("CAS") came up with over 100 commercially available bispyridines from 3 or more suppliers. The following 21 bispyridines were those listed as being available from the largest number of providers. Each one is identified by its CAS registry number, its structure, its chemical composition and its scientific name. It will be appreciated that the list below is intended merely to be exemplary of bispyridines that can be used in the inventive methods and is not intended to be limiting.

1.

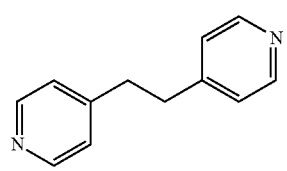

4916-57-8

$C_{12}H_{12}N_2$
Pyridine, 4,4'-(1,2-ethanediyl)bis-

2.

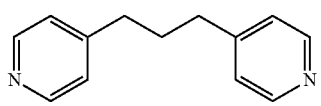

17252-51-6

$C_{13}H_{14}N_2$
Pyridine, 4,4'-(1,3-propanediyl)bis-

3.

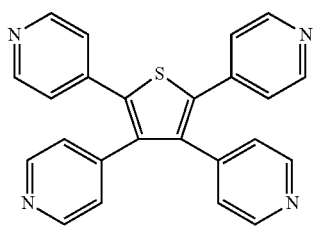

64048-12-0

$C_{24}H_{16}N_4S$
Pyridine, 4,4',4'',4'''-(2,3,4,5-thiophenetetrayl)tetrakis-

4.

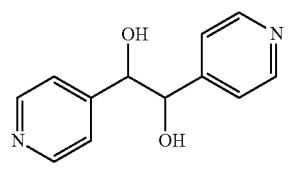

6950-04-5

$C_{12}H_{12}N_2O_2$
1,2-Ethanediol, 1,2-di-4-pyridinyl-

5.

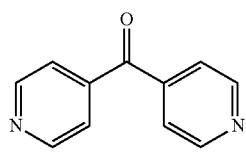

6918-15-6

$C_{11}H_8N_2O$
Methanone, di-4-pyridinyl-

6.

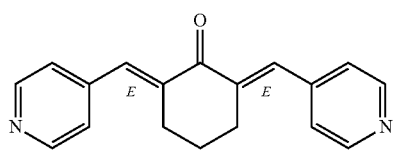

871361-88-5

Double bond geometry as shown.
$C_{18}H_{16}N_2O$
Cyclohexanone, 2,6-bis(4-pyridinylmethylene)-, (2E,6E)-

7.

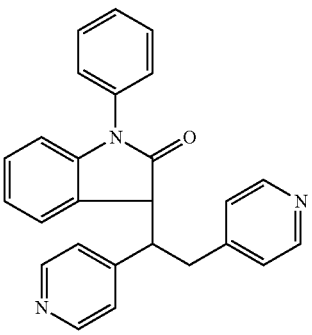

105431-72-9

$C_{26}H_{21}N_3O$
2H-Indol-2-one, 1,3-dihydro-1-phenyl-3,3-bis(4-pyridinylmethyl)-

8.

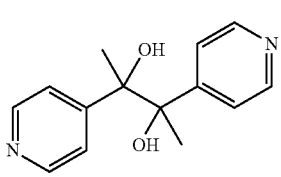

69267-29-4

$C_{14}H_{16}N_2O_2$
2,3-Butanediol, 2,3-di-4-pyridinyl-

-continued 9.  4972-49-0

Relative stereochemistry.
$C_{12}H_{12}N_2O_2$
1,2-Ethanediol, 1,2-di-4-pyridinyl-, (1R,2S)-rel- 10.  122955-42-4

$C_{26}H_{20}N_2O$
9(10H)-Anthracenone, 10,10-bis(4-pyridinylmethyl)-

11.  298685-12-8

$C_{25}H_{24}N_4O_4$
2,4,6(1H,3H,5H)-Pyrimidinetrione, 1-(3-methoxyphenyl)-5,5-bis[2-(4-pyridinyl)ethyl]-

12.  300589-57-5

$C_{20}H_{22}N_4O_3$
2,4,6(1H,3H,5H)-Pyrimidinetrione, 1,3-dimethyl-5,5-bis[2-(4-pyridinyl)ethyl]-

-continued 13.  42899-65-0

$C_{12}H_{10}N_2O$
Ethanone, 1,2-di-4-pyridinyl- 14.  2029-58-5

$C_{14}H_{16}N_2$
Pyridine, 4,4'-(1,4-butanediyl)bis- 15.  346449-67-0

$C_{25}H_{24}N_4O_3$
2,4,6(1H,3H,5H)-Pyrimidinetrione, 1-(phenylmethyl)-5,5-bis[2-(4-pyridinyl)ethyl]-

16.  346449-73-8

$C_{26}H_{26}N_4O_4$
2,4,6(1H,3H,5H)-Pyrimidinetrione, 1-(4-ethoxyphenyl)-5,5-bis[2-(4-pyridinyl)ethyl]-

-continued

17.

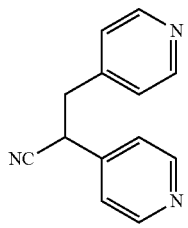

1311317-18-6

$C_{13}H_{11}N_3$
4-Pyridinepropanenitrile, α-4-pyridinyl-

18.

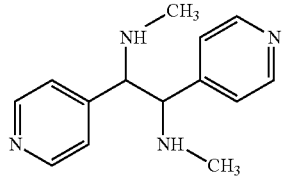

6630-22-4

$C_{14}H_{18}N_4$
1,2-Ethanediamine, N,N'-dimethyl-1,2-di-4-pyridinyl- (9Cl)

19.

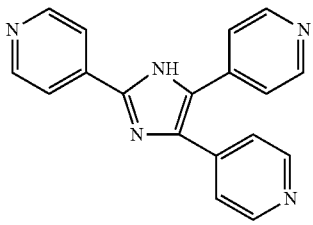

23974-93-8

$C_{18}H_{13}N_5$
Pyridine, 4,4',4''-(1H-imidazole-2,4,5-triyl)tris-

20.

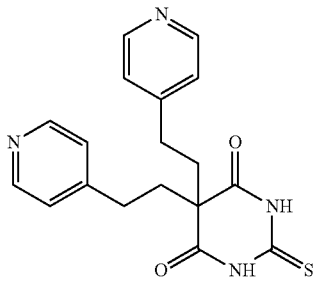

672339-36-5

$C_{18}H_{18}N_4O_2S$
4,6(1H,5H)-Pyrimidinetrione, dihydro-5,5-bis[2-(4-pyridinyl)ethyl]-2-thioxo-

21.

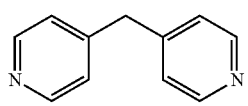

60776-05-8

$C_{11}H_{10}N_2$
Pyridine, 4,4'-methylenebis-

Nucleophile-Reactive Labels

A number of amine-reactive labels are known in the art. The website of Thermo Fisher Scientific (Waltham, Mass.), for example, lists 152 reagents under the label "Amine-Reactive Fluorophores, Biotins, Quantum Dots, & Other Labels," including: 1-pyrenebutanoic acid, succinimidyl ester, 2',7'-Difluorofluorescein (Oregon Green® 488), 5(6)-CR 6G, SE (5-(and-6)-Carboxyrhodamine 6G, Succinimidyl Ester), mixed isomers, and 7-Diethylaminocoumarin-3-Carboxylic Acid. ProZyme, Inc. (Hayward, Calif.) sells a variety of amine-reactive labels, including a basic dye, InstantPC™ (2-(diethylamino)ethyl 4-[(2,5-dioxopyrrolidin-1-yl)oxycarbonylamino]benzoate). Two acid labels disclosed in co-owned U.S. Pat. No. 8,124,792, 8-[(2,5-dioxopyrrolidin-1-yl)oxycarbonylamino]naphthalene-1,3,5-trisulfonic acid ("InstantANTS™") and 4-[(2,5-dioxopyrrolidin-1-yl)oxycarbonylamino]benzoic acid ("InstantAA™"), were used in the Examples reported below. InstantANTS™ adds 3 negative charges and a fluorophore to the glycans, which facilitates their separation by capillary electrophoresis and detection. And, Waters Corporation (Milford, Mass.), sells "RapiFluor-MS™" for labeling glycosylamines. It is anticipated that bispyridines can be used to improve labeling with each of these amine-reactive labels.

Similarly, a large number of thiol-reactive labels are known in the art. The website of Thermo Fisher Scientific, for example, lists 94 reagents under the title "Thiol-Reactive Fluorophores, Biotins & Other Labels", including: BODIPY® 507/545 IA. (N-(4,4-Difluoro-1,3,5,7-Tetramethyl-4-Bora-3a,4a-Diaza-s-Indacene-2-yl) Iodoacetamide, 5-(Bromomethyl)Fluorescein, Alexa Fluor® 350 C5 Maleimide, and DACM, N-(7-Dimethylamino-4-Methylcoumarin-3-yl))Maleimide. It is anticipated that bispyridines can be used to improve labeling with each of these thiol-reactive labels.

Although the compounds discussed above are electrophiles that have been designated by the suppliers to be "amine-reactive" or "thiol-reactive," persons of skill will appreciate that many of the compounds will also label other moieties on nucleophiles of interest, such as guanidine or imidazole groups on proteins or peptides, as well as exocyclic amines on nucleic acids, and can be used to label these nucleophiles. Any particular label can be readily tested to see if it adequately labels any given nucleophile or nucleophilic moiety of interest by running parallel aliquots of the nucleophile, with the label being studied in a first aliquot and a label known to label the nucleophile in a second aliquot, and then analyzing the two aliquots and determining whether the label being studied labels the nucleophile at least as well as the label known to label that nucleophile.

Concentrations

Typically, the bispyridine will be used in a concentration of about 0.5 M to about 2.5M, in some embodiments, will be used at concentrations of about 0.5M to about 2.25M, in some embodiments, will be used at concentrations of about 0.75M to about 2.0M, in some embodiments, will be used at concentrations of about 0.8M to about 1.75M, more preferably at concentrations of about 1M to 1.75M, in some embodiments, will be used at concentrations of about 1M to about 1.5M, and in some embodiments, will be used at concentrations of about 0.8M to about 1.25M, and still more preferably at concentrations of about 1 M, where the term "about" means plus or minus 0.2 M.

Removal of the Bispyridine

In some embodiments, it may be desirable to remove the bispyridine before subjecting the labeled compound to analytical techniques, such as mass spectrometry. The bispyridine can be removed by any convenient means known in the art. In preferred embodiments, the bispyridine is removed by using a solid phase cartridge or other solid phase extraction device used in the art to remove undesired components from a solution. The labeled glycans are typically loaded onto a selected cleanup cartridge, washed to remove most non-glycan contaminants, and then eluted. Cleanup procedures for labeled glycans are routinely used in the art and it is expected that they are well known to practitioners in the art of glycan labeling and analysis.

EXAMPLES

Example 1

This Example sets forth abbreviations for some of the reagents used in exemplar workflows of deglycosylation and labeling procedures performed using exemplar bispyridines in some of the Examples below.

"HEPES": 4-(2-hydroxyethyl)-1-piperazineethanesulfonic acid
"DMF": dimethylformamide
"DMSO": dimethyl sulfoxide
"TMD": Pyridine, 4,4'-(1,3-propanediyl)bis-
"BPE": Pyridine, 4,4'-(1,2-ethanediyl)bis-
"PNGase F mix": a 1:1 mix of PNGase F (~1 mg/ml) and 750 mM HEPES pH 8.0 buffer.

Example 2

This Example sets forth an exemplar workflow for deglycosylating and labeling an amine-reactive compound using an exemplar bispyridine.

Denaturation Step

Twenty μl of 2 mg/ml glycoprotein is added to the bottom of a PCR plate. Two μl of a detergent, such as sodium lauroyl sarcosinate, is added. Optionally, a reductant, such as bis(2-mercaptoethyl) sulfone, can be added. The mixture is incubated for 3 minutes at 90° C.

Enzymatic Digestion Step

Two μl of PNGase F mix is added. The resulting mixture is incubated for 5 mins at 50° C.

Labeling Step

The released glycosylamines are labeled with a dye of choice. The dye is typically a fluorescent dye and in some embodiments is also compatible with mass spectrometry. As an example, the dye can be activated procaine, sold as InstantPC (ProZyme, Inc., Hayward, Calif.). For example, glycans released from a glycoprotein by the action of PNGase F are initially released as glycosamines, which can be labeled by, for example, adding 5 μl of a freshly prepared 1:1 mixture of 0.2 M 2-diethylaminoethyl 4-[(2,5-dioxypyrrolidin-1-yl)oxycarbonylamino]benzoate in DMSO: 1 M TMD. The labeling is allowed to proceed for 2 minutes.

Cleanup Step

If desired, the labeled glycans can be cleaned up before analysis by subjecting them to solid phase extraction, for example, by loading them onto a cartridge, prior to analyzing them by one or more analytic techniques. For example, the cartridge can be washed with 200 μl of a 1:3:96 formic acid:water:acetonitrile solution for 3 minutes at 300×g and the samples eluted with 50 μl of a solution of 200 mM ammonium formate, pH 7, containing 20% DMSO.

Analysis Step

Following elution, glycans released by the PNGase F can be analyzed. For example, 1 μl of eluted sample can be injected for high performance liquid chromatography (HPLC) analysis.

Example 3

This Example reports the effect of studies on the use of bispyridines on labeling of glycosylamines.

An exemplar glycoprotein, porcine gamma globulin, was subjected to enzymatic digestion by an exemplar deglycosylation enzyme, PNGase F. Glycosylamines released from the glycoprotein, containing the buffer HEPES, at pH 8, were labeled using four different amounts, 0.1 μl, 1 μl, 2.5 μl or 5 μl, of an acidic dye, 8-[(2,5-dioxopyrrolidin-1-yl)oxycarbonylamino]naphthalene-1,3,5-trisulfonic acid, at a concentration of 0.2 M, using anhydrous dimethyl sulfoxide ("DMSO") as a solvent, in the presence of 2.5 μl of the following, each of which were also prepared in anhydrous DMSO: (a) 1M Pyridine, 4,4'-(1,3-propanediyl)bis- ("TMD"), (b) 1M Pyridine, 4,4'-(1,2-ethanediyl)bis- ("BPE"), or (c) 1M pyridine ("PYR"). As a control, glycosylamines were also labeled using the same amounts of the dye, but with only the DMSO solvent ("control"). The labeled glycans were analyzed by HPLC and total fluorescent signal was measured using fluorescent wavelengths of 310 nm for excitation and 430 nm for emission.

As shown in FIG. 1, in all of the tests, the amount labeled when pyridine was present in the mixture was very close to that labeled when DMSO was present without pyridine. In contrast, once dye was present in sufficient amounts to label most of the glycosylamines present, the amount labeled in the presence of either bispyridine was surprisingly greater than that labeled by either the control or in the presence of pyridine. When 2.5 μl of dye was present, the presence of BPE increased the amount of labeled glycosylamines by approximately 70% over the amount labeled using only DMSO, while the presence of TMD increased labeled glycan by just under 100%. When 5 μl of dye was used, both BPE and TMD resulted in more than doubling the amount of labeled glycosylamines as shown by relative fluorescent units, or "RFUs".

Example 4

This Example reports the effect of studies to determine the effect of different concentrations of a bispyridine on labeling glycosylamines.

An exemplar glycoprotein, porcine gamma globulin, was subjected to enzymatic digestion by an exemplar deglycosylation enzyme, PNGase F. Glycosylamines released from the glycoprotein were labeled using 2.5 µl of an acidic dye, 4-[(2,5-dioxopyrrolidin-1-yl)oxycarbonylamino]benzoic acid, at a concentration of 0.2 M, using anhydrous dimethylforamide ("DMF") as a solvent, in the presence of (a) DMF alone, as a control, (b) 2.5 µl of 4 M TMD, or (c) 1 M TMD. The labeled glycans were analyzed by HPLC and total fluorescent signal was measured using fluorescent wavelengths of 380 nm for excitation and 430 nm for emission.

Figure 2:
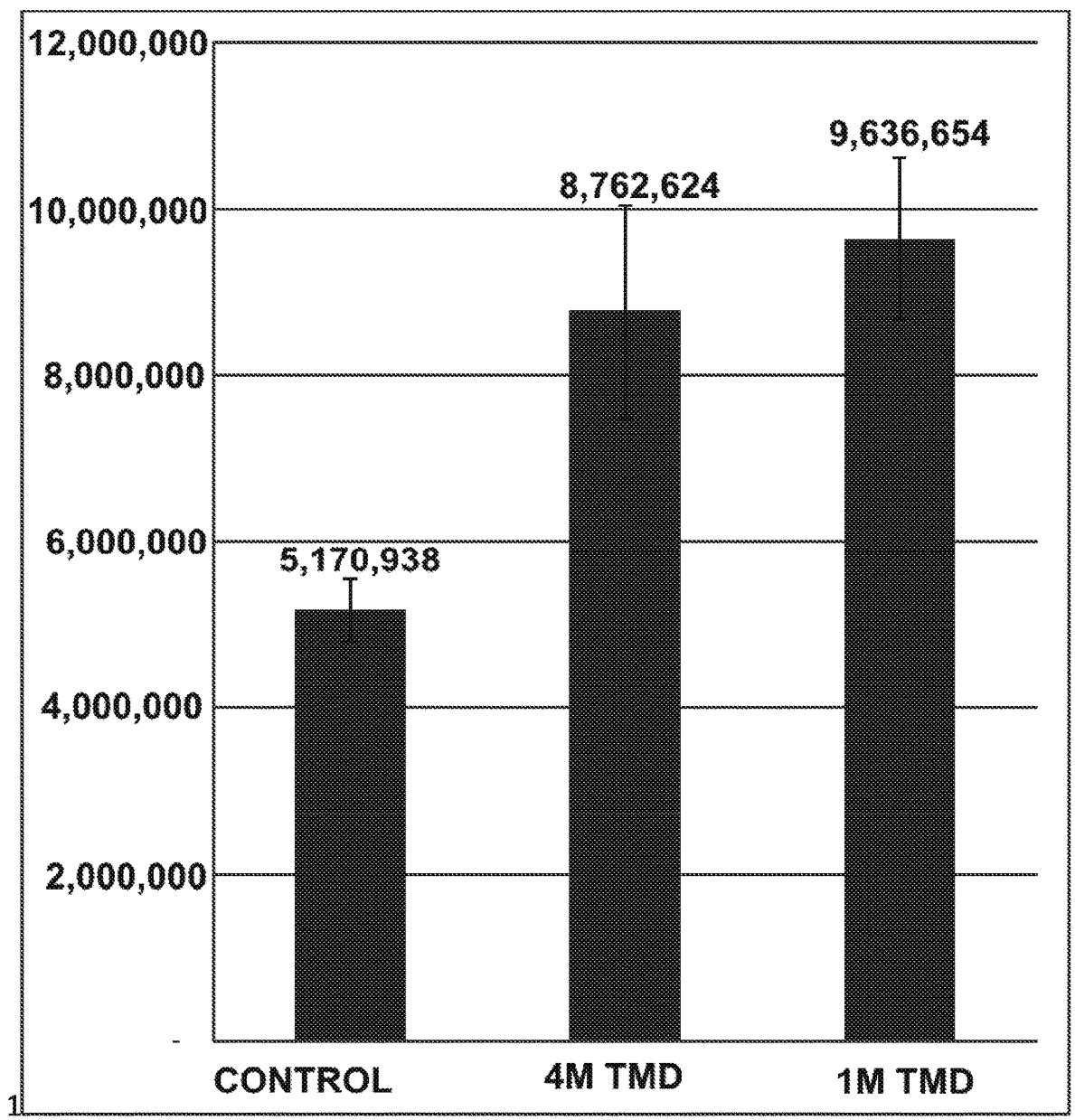
FIG. 2 is a graph showing the total glycan signal of labeled glycosylamines released by PNGase F from an exemplar glycoprotein, porcine gamma globulin, labeled by a different acidic dye, 4-[(2,5-dioxopyrrolidin-1-yl)oxycarbonylamino]benzoic acid, in the presence of either 1M Pyridine, 4,4'-(1,3-propanediyl)bis- ("TMD") dissolved in anhydrous dimethylforamide ("DMF"), 4M TMD in DMF, or DMF without TMD ("control"). Vertical axis: total glycan signal, in RFUs, measured at 430 nm. Horizontal axis: The bars show the average value of RFUs in the presence of the control or stated concentration of TMD, with the numeric value of the average stated above the bar for ready comparison. The error bars show one standard deviation.

As shown in FIG. 2, the use of 1 M TMD resulted in just under twice the amount of labeled glycosylamines as did the use of the control, solvent alone. The use of 4 M TMD resulted in over a 69% increase of labeled glycosylamines, while the use of 1 M TMD resulted over an 86% increase in labeled glycosylamines. For convenience, the average reading of the amount of labeled glycosylamines is shown numerically in FIG. 2 over each bar, with the error bars showing 1 standard deviation.

Example 5

This Example reports the effect of studies to determine optimal concentrations of a bispyridine on labeling glycosylamines.

Figure 3:
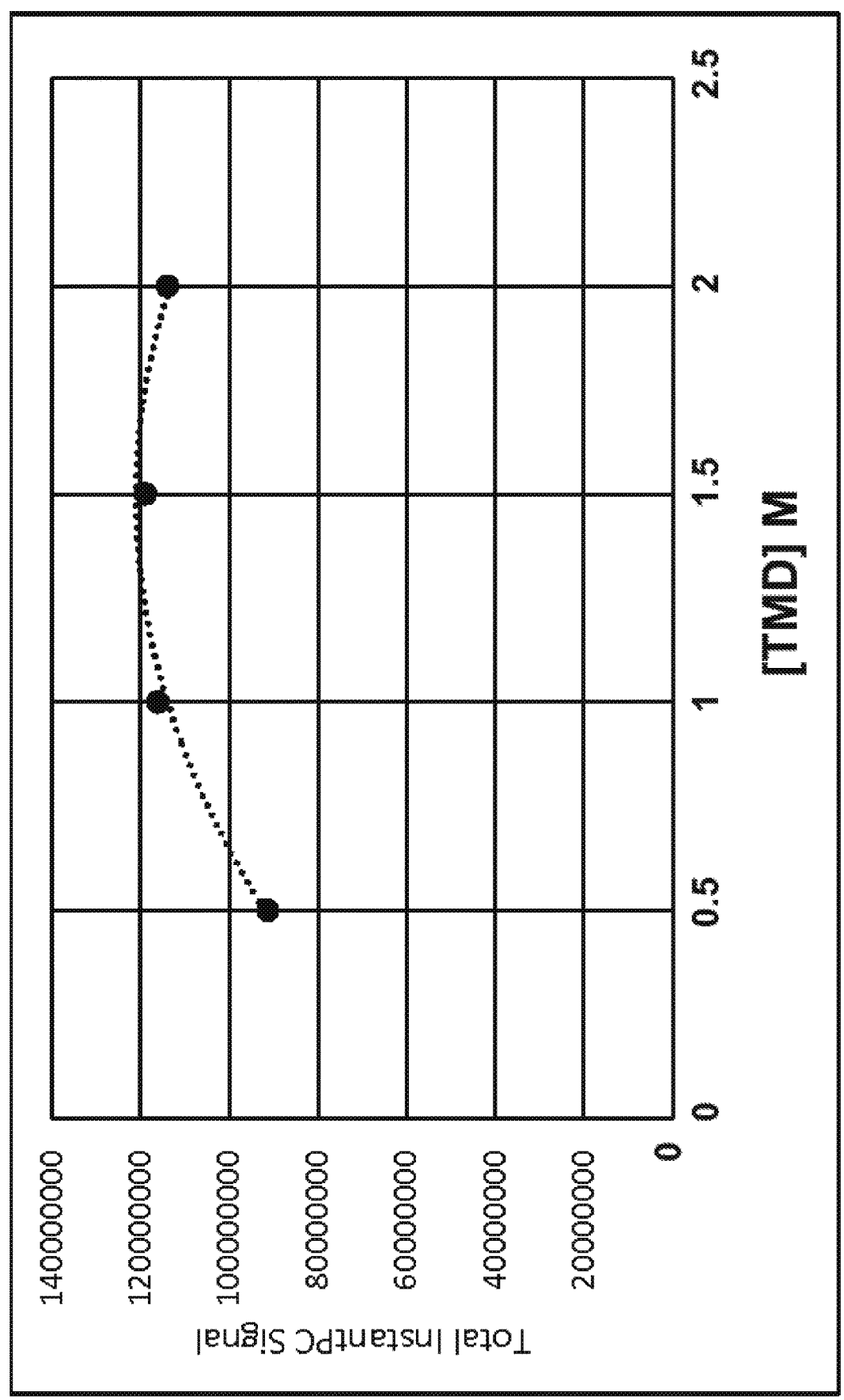
FIG. 3 is a graph showing a ranging study of the effect of the concentration of TMD on total glycan signal. Glycosylamines released by PNGase F from porcine gamma globulin were labeled with a basic dye, InstantPC,™ dissolved in anhydrous DMSO, and analyzed by HPLC, with total fluorescent signal measured at 345 nm. Vertical axis: circles show the glycan signal, in RFUs for each concentration of TMD tested. Horizontal axis: Molar concentrations of TMD tested.

The exemplar glycoprotein, porcine gamma globulin, was subjected to enzymatic digestion by the exemplar deglycosylation enzyme, PNGase F. Glycosylamines released from the glycoprotein were labeled using 2.5 µl of the basic dye InstantPC™ (ProZyme, Inc., Hayward, Calif.) at a concentration of 0.2 M in DMF, mixed with 2.5 µl of 0.5, 1, 1.5, or 2 M TMD. The labeled glycans were then analyzed by HPLC and total fluorescent signal was measured using fluorescent wavelengths of 285 nm for excitation and 345 nm for emission. As shown in FIG. 3, very similar amounts of labeling were seen using 1 M, 1.5 M, and 2 M TMD with this dye.

Example 6

This Example sets forth an exemplar protocol for preparing a solution for labeling an exemplar nucleophile, a glycosylamine, with an exemplar basic label in a solution containing an exemplar bispyridine.

A solution of 0.5M TMD in anhydrous DMF is prepared. 150 µl of this solution is added to 30 mg of dry InstantPC™ (2-(diethylamino)ethyl 4-[(2,5-dioxopyrrolidin-1-yl)oxycarbonylamino]benzoate). Five µl of this solution (InstantPC™ with 0.5M TMD in DMF) is added to 25 µl of a protein digest containing glycosylamines in HEPES buffer pH 8.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:
1. A method of labeling N-glycans released from a glycoprotein of interest, said method comprising:
 (a) incubating said glycoprotein with an enzyme that releases said N-glycans from said glycoprotein as glycosylamines, and
 (b) contacting said glycosylamines with a solution comprising a solvent, an amine-reactive label, and a bispyridine, under conditions allowing labeling of said glycosylamines by said amine-reactive label,
thereby labeling said N-glycans released from said glycoprotein with said amine-reactive label.
2. The method of claim 1, wherein said glycoprotein is an antibody.
3. The method of claim 1, further wherein said glycoprotein is immobilized on a solid support before step (b).
4. The method of claim 1, wherein said enzyme is an endoglycosidase.
5. The method of claim 4, further wherein said enzyme is an amidase.
6. The method of claim 5, further wherein said amidase is PNG F.
7. The method of claim 1, wherein said solvent is dimethylforamide or dimethyl sulfoxide.
8. The method of claim 1, wherein said bispyridine is pyridine, 4,4'-(1,3-propanediyl)bis- or pyridine, 4,4'-(1,2-ethanediyl)bis-.
9. The method of claim 1, further wherein said labeled glycosylamines are provided to an analytical means.
10. The method of claim 9, wherein said analytical means is selected from the group consisting of high-pressure liquid chromatography, capillary electrophoresis, microfluidic separation, and mass spectrometry.
11. The method of claim 10, wherein said analytical means is high-pressure liquid chromatography.
12. The method of claim 10, wherein said analytical means is mass spectrometry.
13. The method of claim 1, wherein said bispyridine is pyridine, 4,4',4",4'" (2,3,4,5-thiophenetetrayl)tetrakis; 1,2-Ethanediol, 1,2-di-4-pyridinyl; methanone, di-4-pyridinyl; cyclohexanone, 2,6-bis(4-pyridinylmethylene-,(2E6E)-; 2H-Indol-2-one, 1,3-dihydro-1-phenyl-3,3-bis(4-pyridinylmethyl)-; 2,3-Butanediol, 2,3-di-4-pyridinyl-; 1,2-Ethanediol, 1,2-di-4-pyridinyl-, (1R,2S)-rel-; 9(10H)-Anthracenone, 10,10-bis(4-pyridinylmethyl)-; 2,4,6(1H,3H,5H)-Pyrimidinetrione, 1-(3-methoxyphenyl)-5,5-bis[2-(4-pyridinyl)ethyl]-; 2,4,6(1H,3H,5H)-Pyrimidinetrione, 1,3-dimethyl-5,5-bis[2-(4-pyridinyl)ethyl]-; Ethanone, 1,2-di-4-pyridinyl-; Pyridine, 4,4'-(1,4-butanediyl)bis-; 2,4,6(1H,3H,5H)-Pyrimidinetrione, 1-(phenylmethyl)-5,5-bis[2-(4-pyridinyl)ethyl]-; 2,4,6(1H,3H,5H)-Pyrimidinetrione, 1-(4-ethoxyphenyl)-5,5-bis[2-(4-pyridinyl)ethyl]-; 4-Pyridinepropanenitrile, α-4-pyridinyl-; 1,2-Ethanediarnine, N,N'-dimethyl-1,2-di-4-pyridinyl-(9Cl); pyridine, 4,4',4"-(1H-irnidazole-2,4,5-triyl)tris-; 4,6(1H,5H)Pyrimidinedione, dihydro-5,5-bis[2-(4-pyridinyl)ethyl]-2-thioxo-; or Pyridine, 4,4'-methylenebis-.

* * * * *